United States Patent [19]
Buckles et al.

[11] 4,140,117
[45] Feb. 20, 1979

[54] CARTRIDGE FOR LIQUID INFUSION APPARATUS

[75] Inventors: Richard G. Buckles, Redwood City; Seymour Hoff; Sharon Kehr, both of San Jose; Su Il Yum, Mountain View, all of Calif.

[73] Assignee: Alza Corporation, Palo Alto, Calif.

[21] Appl. No.: 798,507

[22] Filed: May 19, 1977

Related U.S. Application Data

[63] Continuation of Ser. No. 576,844, May 12, 1975, abandoned, which is a continuation-in-part of Ser. No. 439,137, Feb. 4, 1974, Pat. No. 3,895,631.

[51] Int. Cl.² .................................................. A61J 7/00
[52] U.S. Cl. .................................. 128/213 R; 222/50; 128/214 F; 128/DIG. 12; 128/218 A
[58] Field of Search ............ 128/218 A, 218 D, 214.2, 128/213, 214 R, 214 F, DIG. 1, DIG. 6, DIG. 26, 218 DA; 222/386.5, 95, 105, 206, 207, 23, 47

[56] References Cited

U.S. PATENT DOCUMENTS

| | | | |
|---|---|---|---|
| 1,235,550 | 8/1917 | Carmody | 222/386.5 |
| 3,008,476 | 11/1961 | Pepin | 222/386.5 X |
| 3,017,883 | 1/1962 | Dickinson | 128/272 |
| 3,048,171 | 8/1962 | Grau | 128/DIG. 12 |
| 3,225,967 | 12/1965 | Heimgartner | 222/206 X |
| 3,677,246 | 7/1972 | Stein | 128/218 D X |
| 3,731,679 | 5/1973 | Wilhelmson et al. | 128/214 F |
| 3,848,593 | 11/1974 | Baldwin | 128/218 DA |
| 3,858,581 | 1/1975 | Kamen | 128/DIG. 1 X |
| 3,895,741 | 7/1975 | Nugent | 128/214 F X |

*Primary Examiner*—Richard C. Pinkham
*Assistant Examiner*—William R. Browne
*Attorney, Agent, or Firm*—Thomas E. Ciotti; Paul L. Sabatine; Edward L. Mandell

[57] ABSTRACT

A removable cartridge that is used in combination with a liquid drug infusion apparatus that comprises a housing that defines an inlet and outlet and has a recess for receiving the cartridge, a confined flow passageway extending between the inlet and outlet, and a conduit extending from the outlet to the infusion site. The removable cartridge includes: a hollow shell that fits within the recess, is adapted to contain the liquid drug, and has an outlet that is adapted to communicate with the inlet of the housing and the drug contained within the shell; pressure means within the shell that maintains a constant, positive pressure on the drug; and lock means on the shell that engages the housing to reversibly lock the cartridge within the recess.

5 Claims, 8 Drawing Figures

CARTRIDGE FOR LIQUID INFUSION APPARATUS

CROSS-REFERENCE TO RELATED APPLICATIONS

This application is a continuation of copending application Ser. No. 576,844 filed May 12, 1975 and since abandoned which in turn is a continuation-in-part of application Ser. No. 439,137 filed Feb. 4, 1974, now U.S. Pat. No. 3,895,631.

BACKGROUND OF THE INVENTION

1. Field of the Invention

The invention is a removable cartridge for use in combination with a liquid infusion apparatus that may be used to infuse liquid drug continuously into a patient.

2. Description of the Prior Art

Assemblies that hold liquid and are adapted to be detachably connected to an infusion system and provide the source of liquid to be infused are known. Generally, there are two types of assemblies: those that are affixed directly to an end of the infusion system such as the assemblies described in U.S. Pat. Nos. 2,703,084 and 3,486,539; and those that are remotely connected to the system by a conduit, such as the assemblies described in U.S. Pat. Nos. 3,451,393 and 3,731,679.

SUMMARY OF THE INVENTION

The invention is a removable, replaceable, cartridge adapted to hold liquid drug and to be used in combination with a particular infusion apparatus.

The infusion apparatus comprises: a housing that defines an inlet port and an outlet port and that has a recess for receiving the cartridge, a flow passageway confined within the housing extending between the inlet port and the outlet port; and a conduit connected to the outlet port and extending therefrom to the infusion site. The housing will normally be adapted to be removably affixed to a patient, but it may alternatively be adapted to be affixed to the patient's bed, bedside stand or the like. There will also normally be a flow control element within the flow passageway.

The cartridge comprises: a hollow shell that is adapted to fit within the recess in the infusion apparatus housing, is adapted to contain the liquid drug, and has an outlet that is adapted to communicate with the inlet port of the infusion apparatus housing to permit the liquid drug to flow from within the shell into the flow passageway within the housing; pressure means within the shell for maintaining a substantially constant, positive pressure on the liquid drug within the shell; and lock means on the shell for engaging the housing to reversibly lock the cartridge within the recess in the infusion apparatus housing.

Preferred embodiments of the cartridge have a shell whose exterior surface forms a substantially unbroken, smooth surface with the exterior surface of the housing when the cartridge is locked within the housing recess. They also include: a collapsible container that is housed in the shell whose interior contains the liquid drug and is connected to the shell outlet and that collapses in response to the pressure generated by the pressure means; and a valve in the shell outlet that is normally closed when the cartridge is not locked within the recess and is opened by the communication with the inlet port of the housing when the cartridge is locked within the recess.

In particularly preferred embodiments, the collapsible container is an elastomeric, axially and radially distensible bladder, the elastic force is the walls of which comprise the pressure means. Such embodiments also include means for indicating the volume of liquid drug in the bladder and a visible volume scale on the shell. The position of the indicator relative to the scale as the former moves relative to the latter as the bladder is inflated or deflated indicates said volume.

As used herein and in the claims, the term "liquid drug" includes drugs that are liquid in their natural form, solutions of drugs and other liquid formulations of drugs.

DETAILED DESCRIPTION OF THE INVENTION

Figure 1:
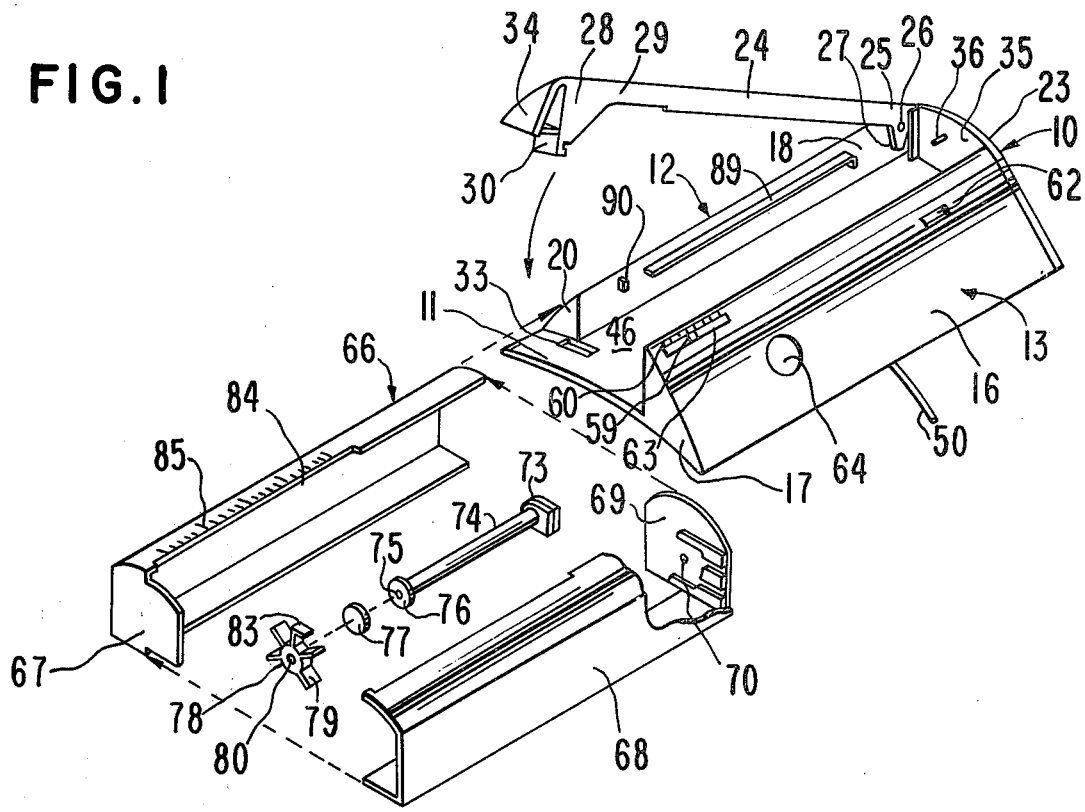
FIG. 1 is an exploded, dimetric view of one embodiment of the infusion apparatus with a portion of the cartridge broken away.
Figure 2:
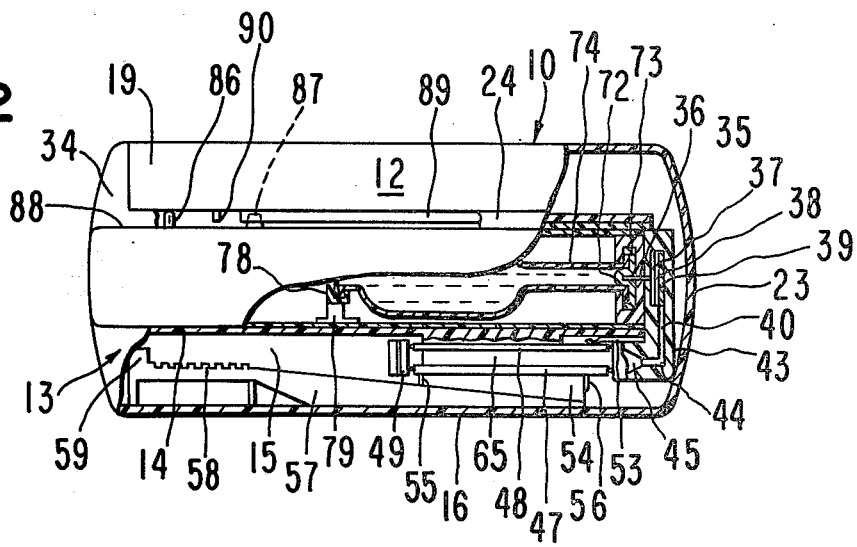
FIG. 2 is a top plan view of the apparatus of FIG. 1 with certain parts broken away and certain parts shown in section.

The embodiment of the infusion apparatus shown in FIGS. 1 and 2 includes a main housing 10 having a generally rectangular support base 11 upon which are mounted the various sub-assemblies comprising the complete apparatus. Support base 11 is preferably slightly curved to conform the curvature of either a particular portion of the torso of a patient or an extremity such as an arm or a leg. The apparatus is particularly well suited for use on the arm or leg of a patient, and in order to maintain it in position thereon, it is equipped with suitable attaching means (not shown), such as a pair of adjustable elastic bands affixed to the underside of base 11; plastic or metallic clips or bracelets; belts or straps provided with cloth fasteners, zippers, or buckles; or elastic or inelastic ties or adhesive tapes.

Mounted on support base 11 are two spaced, elongated housing sections 12 and 13 each having a generally triangular cross section as shown in FIG. 1. Section 13 is defined by a generally flat, upright interior wall 14, an outwardly and downwardly inclined floor 15, and a generally flat inclined outer wall 16. The end of section 13, to the left as seen in FIG. 1, is closed by a wall 17 whose periphery joins with walls 14, 16 and the support base 11.

Section 12 has along its inner side a generally upright wall 18 that extends from support base 11 to the upper edge of a flat, inclined outer wall 19 that joins base 11 along its longitudinal edge. The left end of section 12, as seen in FIG. 1, is closed by an upright wall 20, with the opposite end of section 12 open and recessed from the edge of support base 11 in a manner similar to that of section 13. A convex wall 23 of generally triangular configuration has a smoothly rounded, inwardly directed flange formed about its upper periphery and closes the right end of the apparatus by joining wall 16 and 19 with support base 11.

A locking lever 24 is journalled at an end 25 for pivotal rotation about a pin 26 protruding inwardly from wall 18 of section 12. End 25 further supports a flange 27 for cooperative engagement with a protrusion (not shown) on wall 18 so as to limit the degree of upward swing of lever 24 away from support base 11. The other end 28 of lever 24 carries a downwardly extending, generally flat plate 29. A locking tang 30 protrudes laterally below the bottom edge of plate 29 for cooperative engagement with an aperture 33 in support base 11. Lever 24 also has a generally triangular, curved outer wall 34 that acts as a handle and is shaped such that lever 24, when in a closed or locked position, is contiguous at its outer surface boundaries with the outer surfaces of section 12.

As seen in FIG. 2, there is a fluid flow passageway confined within the right end of the apparatus. The inlet to the passageway is defined by a hollow, needle-like profusion 36. The hollow of protrusion 36 feeds into a chamber 37 defined by a housing element 35. Spaced from the left wall of chamber 37 by an O-ring 38 is a filter assembly 39 consisting of one or more filters designed to retain small particles or sediment and bacteria and preclude the passage of the same through the downstream portions of the flow control assembly.

Downstream of filter assembly 39 is a flow passage 40 defined by a groove in the outer wall of element 35 and a flat plate 43 attached thereover. Passage 40 extends through an elbow 44 in element 35 and diverges outwardly to provide an interior chamber 45. It is noted that element 35 is constructed so as to join with base 11, the edge of end wall 23, and walls 14 and 18 at the right ends of sections 12 and 13. Element 35 thus functions as an end wall of the generally rectangular recess 46 on top of base 11 between sections 12 and 13 and closes off the compartment joining sections 12 and 13.

Chamber 45 feeds into two spaced, fluid carrying conduits 47 and 48, that are mounted on floor 15 and connected at one of their ends in fluid-tight engagement to chamber 45. An upstanding wall 65 extends longitudinally in the space between conduits 47 and 48. The opposite ends of conduits 47 and 48 are connected in fluid-tight engagement to a hollow connecting block 49 also mounted on floor 15. The hollow of connector block 49 is connected to one end of a flexible surgical tube 50 that extends through the bottom of the apparatus to the exterior thereof. The other end of tube 50 is connected with a catheter or needle (not shown) for infusion of the liquid drug to a patient.

Conduit 47 taken together with wedges 54, 57 comprise a fluid flow control such as is described in U.S. Pat. No. 3,031,600 issued Aug. 27, 1974. Briefly, conduit 47 contains a plurality of axially aligned fibers (not shown) that occupy a substantial portion of the space within conduit 47. Compression of conduit 47 between wedge 54 and wall 65 decreases the volume within conduit 47 available for fluid flow. Such compression is achieved via longitudinal movement of wedge 57 to the right, thereby displacing wedge 54 upwardly (as seen in FIG. 2) into engagement with conduit 47. Longitudinal movement of wedge 54 is prevented by upstanding stops 55, 56 mounted on floor 15. Longitudinal movement of wedge 57 may be accomplished by cooperative engagement between rack gear 58 on the left end of wedge 57 and a pinion gear tool (not shown) that is adapted to extend through aperture 64 in wall 16 and engage rack gear 58. A pointing arm 59 extends from the left end of rack gear 58 and has a scribed line for cooperation with a flow rate scale 60 on the outside of wall 16 (FIG. 1). Pointer 59 can be seen through an opening 63 in wall 16 and, since the longitudinal position of rack 58 determines the position of wedge 54 relative to conduit 47, indicates the flow rate setting of fluid being dispensed through the infusion apparatus.

Conduit 48 is a bypass of conduit 47. It may be used to bleed air from the flow passageway when the apparatus is initially prepared for use or to rapidly infuse the drug into the patient. This bypass mechanism is operated by a spring 53 that is adjacent to elbow 44 in floor 15 of section 13 and has at its distal end an offset, curved portion that engages conduit 48. Spring 53 exerts a biasing force against conduit 48 so as to pinch the same between its curved offset portion and the side of wall 65. Thus, spring 53 normally precludes the passage of fluid through conduit 48 and enables fluid flow therethrough only when it is lifted away from wall 65. Aperture 62 in wall 16 provides access to spring 53 to lift it away.

The removable cartridge of infusion apparatus 10 is best seen in FIG. 1. Cartridge assembly 66 is formed of left and right cartridge halves 67 and 68, respectively, has a generally rectangular cross section, and conforms to recess 46 between sections 12 and 13. The upper surfaces of halves 67 and 68 are slightly curved such that when the cartridge is placed in recess 46 and lever 24 is pivoted to its locked position, the overall apparatus has a substantially smooth, substantially unbroken, outer surface as shown in FIG. 1. Half 68 has an end wall 69 defining an aperture 70. Aligned over aperture 70 is a valve assembly 73 of a distensible, elastomeric fluid-containing bladder 74. Valve assembly 73 is attached to wall 69 in any suitable manner such as by means of clamps, bolts, or interlocking grooves (not shown).

The basic element of valve assembly 73 is a flat, resilient member 72 (FIG. 2) that is urged by the internal pressure within the bladder into a closed position in sealed engagement with wall 69 when the cartridge is removed from the apparatus, and into an open position (as in FIG. 2) by engagement with protrusion 36 when the cartridge is in position within recess 46.

The opposite end of bladder 74 defines an opening 75 having an annular flange 76. Aligned over opening 75 against the surface of flange 76 is a microfilter 77 which allows the passage of air but not fluid. Microfilter 77 is firmly clamped between flange 76 and the inner flat surface of a sliding spider 78 having a plurality of arms 79 extending radially from a central hub. Arms 79 are preferably engaged with the four inner corners of the rectangular shell provided by halves 67 and 68 of cartridge 66 such that the spider is freely slidable longitudinally within the shell. An aperture 80 extends completely through the central hub of spider 78 such that air passing through filter 77 may be expelled to the atmosphere. A generally L-shaped indicating arm 83 protrudes upwardly from the central hub of spider 78 and has a first leg that extends over a recessed path 84 longitudinally disposed along a central portion of half 67. A volume scale 85 is imprinted upon the upper surface of half 67 and cooperates with indicator arm 83 to indicate the volume of drug in the bladder 74.

Bladder 74 may be distended by the admission of fluid under pressure through valve 73 such that the bladder is axially and radially enlarged, as shown in FIG. 2, for storing the drug under pressure. As the drug is forced into bladder 74, the bladder becomes axially elongated such that spider 78 slides toward the end away from the valve 73, with pointer 83 indicating the volume of drug admitted on scale 85. In addition, since bladder 74 is supported between valve assembly 73 attached to wall 69 of cartridge 66 and the spider 78, the same is at all times spaced from the inner walls of halves 67, 68 to allow precise delivery of the entire contents of the bladder with minimal frictional interference. Furthermore, the distensible elastic wall of bladder 74 is constructed so that it distends radially only to approximately the inner dimensions of the cartridge 66. Therefore, even when fully distended, it does not engage the inner walls of halves 67, 68. The elastic force inherent in the walls of bladder 74 provides a constant pressure on the liquid drug of sufficient magnitude to deflate the bladder and infuse the drug into the patient at a desired flow rate.

Three pins, one designated 86, the second designated 87, and the third not shown, protrude from the side wall 88 of half 67 of cartridge 66. Pin 86 is adapted to cooperatively engage the inner edge of plate 29; pin 87 is adapted to be positioned beneath lever support bar 89; and the third pin (not shown) is adapted to cooperatively engage flange 27. Thus as cartridge 66 is lowered into recess 46 with pin 87 passing between stop 90 and the left end of bar 89 and slid to the right along base 11, pin 87 slips underneath bar 89 and the third pin engages flange 27 and causes lever 24 to lower. Further downward rotation of lever 24 causes pin 86 to engage the inner edge of plate 29, thereby urging cartridge 66 into a firmly nested position in recess 46 with protrusion 36 extending through aperture 70 and opening valve 73. Cartridge 66 is reversibly locked into recess 46 by snapping tang 30 into aperture 33.

Figure 3:
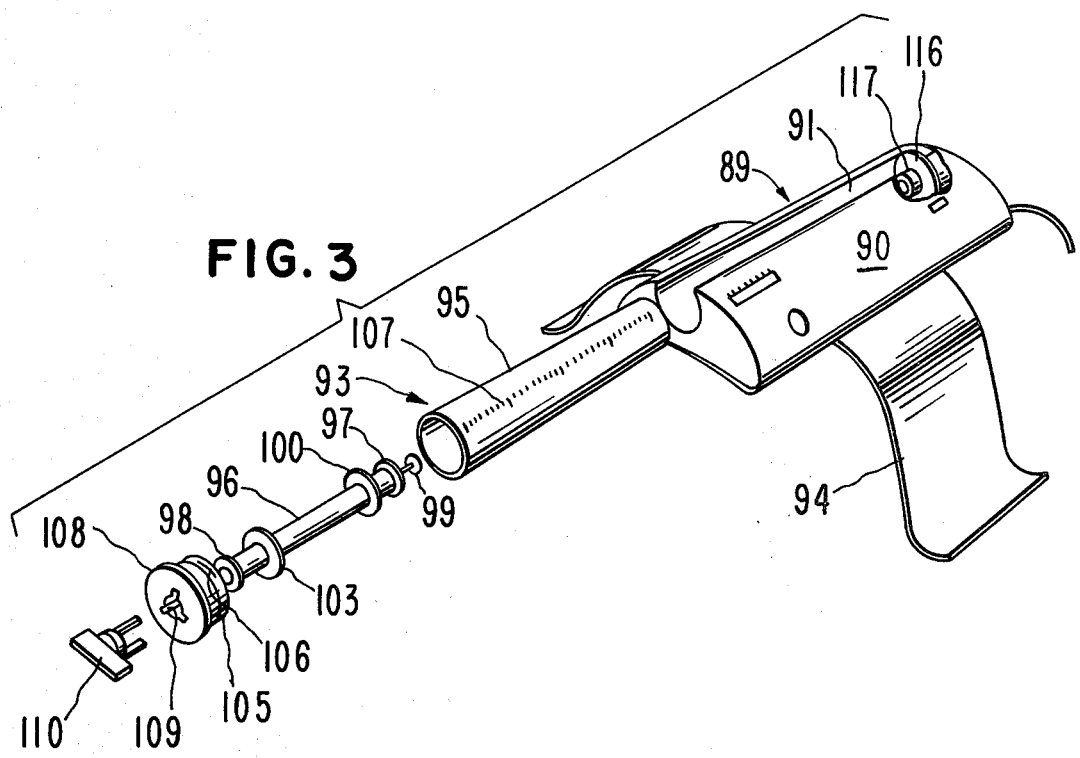
FIG. 3 is an exploded, dimetric view of another embodiment of the infusion apparatus with a portion of the housing broken away.
Figure 4:
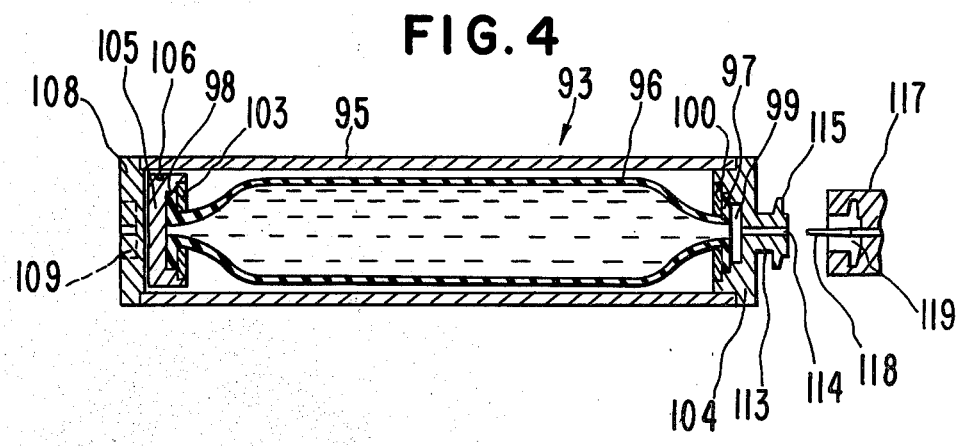
FIG. 4 is an enlarged top, plan, sectional view of the cartridge of the apparatus of FIG. 3 and a portion of the apparatus that mates with the cartridge.

FIGS. 3 and 4 illustrate another embodiment of the infusion apparatus. This embodiment is generally designated 89. Apparatus 89 is essentially identical to apparatus 10 except in the following features: the shapes of the cartridge shell and the recess in the housing into which it is received; and the interlock means between the housing and the cartridge. Accordingly, only these features are described in detail.

Apparatus 89 basically comprises a housing 90 having a recess 91 of partially circular cross section in its top surface, and a cartridge, generally designated 93. Housing 90 contains a flow passageway and flow control assembly as does the housing of apparatus 10. A strap 94 is affixed to housing 90 for affixing the apparatus to a patient. Cartridge 93 includes a tubular cylindrical shell 95 that is sized to slide snugly into recess 91 with the exposed portion of the shell forming a continuous smooth surface together with the exterior of housing 90. Contained within shell 95 is a tubular elastomeric bladder 96 identical to bladder 74 of cartridge 66. Flanges 97 and 98 are affixed to either end of bladder 74 and a standard aerosol flow valve 99 is fitted in fluid-tight engagement into the right end of bladder 74. A pair of sealing rings 100, 103 are positioned about bladder 74 inwardly of flanges 97 and 98 for attaching the ends of the bladder 74 to a cartridge end wall 104 and a slidable, bladder sealing member 105, respectively. Member 105 is free to slide axially within shell 95 as the bladder 96 is inflated and deflated. Member 105 is scribed at 106 and the scribing cooperates with a volume scale 107 on shell 95 to indicate the volume of fluid in the bladder 96, which volume is correlated to the axial extension of bladder 96 within shell 95. An end cap 108 closes the outer (left) end of cartridge 93. Cap 108 has a keyway 109 in it that is adapted to receive a key 110.

End wall 104 of cartridge 93 has an axial stud 113 extending outwardly from its exterior surface and a central, axial bore 114 extending completely through it. Stud 113 has a male thread 115 on its outer end. As seen in FIG. 3, the housing is fitted, at the inner (right) end of recess 91, with a flow passage element 116 that functions similarly to element 35 of apparatus 10. Element 116 has a boss 117 on it that extends into recess 91 and a hollow, needle-like protrusion (FIG. 4) 118 that functions as the inlet to the flow passageway of the apparatus. Boss 117 has a female threaded bore 119 that is adapted to receive stud 113 in interlocking relationship. This is, when cartridge 93 is slid into recess 91, stud 113 is received in bore 119. Key 110 is then inserted into keyway 109 and the cartridge is rotated to turn the male thread of stud 113 into locked position within the female thread of bore 119. The cartridge may be removed from the apparatus by simply rotating the cartridge in the opposite direction with key 110 to disengage said threads and sliding the cartridge back out of recess 91.

As stud 113 is received within bore 119, protrusion 118 is received within bore 114 of stud 113 and the tip of protrusion 118 engages and depresses flow valve 99 thereby opening it and permitting flow of drug from bladder 96 into the flow passageway of apparatus 99 and thence to the patient. When the cartridge is removed from recess 91 as described above, protrusion 119 disengages flow valve 99 and the pressure from the drug within the bladder 96 will force the valve 99 against the inner surface of end wall 104, thereby closing valve 99.

FIGS. 5–8 illustrate alternatives to cartridge 93. The cartridges of FIGS. 5–8 are identical in all respects to cartridge 93 except in the means by which pressure is applied to the liquid drug within the cartridge. Accordingly, only this feature of these cartridges is described in detail.

Figure 5:
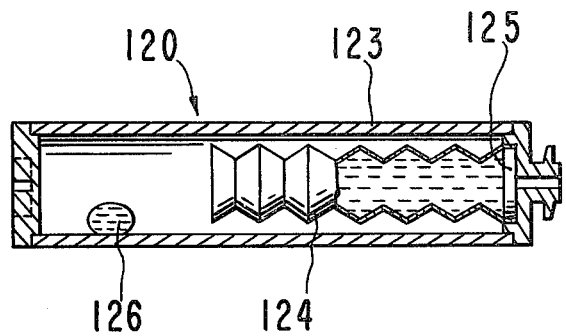
FIGS. 5-8 are sectional views of alternative cartridges to the cartridge of FIG. 4. A portion of the cartridge of FIG. 5 is broken away and a portion of the cartridge of FIG. 8 is shown schematically.

The cartridge of FIG. 5, generally designated 120, comprises a tubular shell 123 that is hermetically sealed. Confined within shell 123 is an axially collapsible, fluid-tight bellows 124 that contains the drug charge. The leading (right) end of bellows 124 is fitted with a valve assembly 125 identical to valve assembly 99 of cartridge 93. A small portion of a liquid 126 is contained within shell 123 exteriorly of bellows 124. Liquid 126 has a vapor pressure in excess of atmospheric pressure at the temperature at which the cartridge is used. Accordingly, the vapor pressure of liquid 126 exerts a constant, deflating force on bellows 124 of sufficient magnitude to overcome the pressure drop through the infusion apparatus and infuse the drug into a patient.

Figure 6:
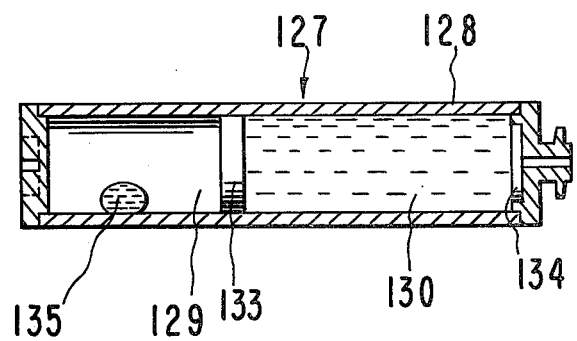

FIG. 6 also shows a cartridge, generally designated 127, in which the pressure is exerted on the drug charge by vapor pressure. Cartridge 127 comprises a hermetically sealed, tubular shell 128. The hollow interior of shell 128 is divided into two compartments, 129, 130 that are separated by a fluid-tight, axially slidable piston 133. The liquid drug charge is contained within compartment 130 and the right end of compartment 130 is fitted with a valve assembly 134 identical to the valve assembly of the cartridge of FIGS. 3 and 4. A small portion of a liquid 135 is contained within compartment 129. Liquid 135 has a vapor pressure in excess of atmospheric pressure at the temperature at which cartridge 127 is used. This vapor pressure exerts a force on the left hand side of piston 133 which in turn exerts a discharging force on the liquid drug within compartment 130.

Figure 7:
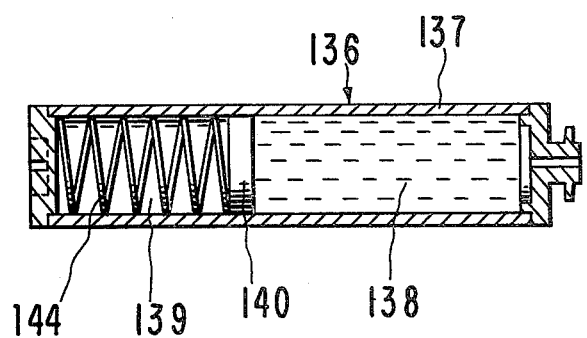

FIG. 7 depicts a cartridge, generally designated 136, in which pressure is exerted on the drug charge solely by mechanical means. Cartridge 136 comprises a fluid-tight, tubular shell 137 whose hollow interior is separated into two compartments 138, 139 by a fluid-tight, axially slidable piston 140. Compartment 138 contains the liquid drug charge and its right hand end is fitted with a valve assembly 143 identical to the valve assembly of the cartridge of FIGS. 3 and 4. Compartment 139 houses a spring 144 that is under significant compression and thus exerts an essentially constant force on piston 140 which in turn exerts discharging pressure on the drug charge within compartment 138.

Figure 8:
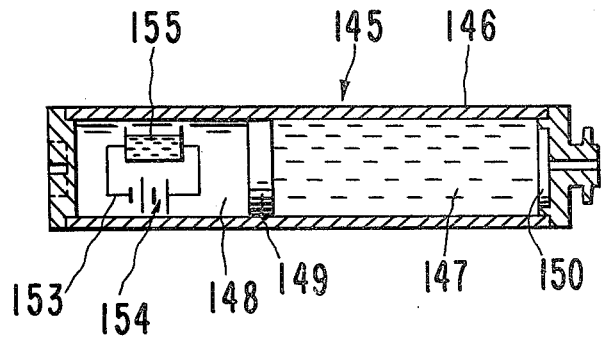

FIG. 8 illustrates a cartridge, generally designated 145, in which the pressure is exerted upon the liquid drug by a gas that is generated by electrolysis. Cartridge 145 comprises a hermetically sealed, tubular shell 146 whose hollow interior is separated into two compartments 147, 148 by a fluid-tight, axially slidable piston 149. Compartment 147 contains the drug charge and its right hand end is fitted with a valve assembly 150 identical to the valve assembly of the cartridge of FIGS. 3 and 4. Compartment 148 houses a small electrolysis cell (illustrated schematically) 153 that includes a source of electricity 154 and an appropriate electrolyte solution 155. Cell 153 generates a gas, such as hydrogen, at a constant rate, thereby producing a constant pressure on piston 149 which in turn exerts discharging pressure on the drug within compartment 147.

Modifications of the above described infusion apparatuses and cartridges that are obvious to those of skill in the mechanical and/or medical apparatus arts are intended to be within the scope of the following claims.

We claim:

1. A removable cartridge for use in combination with a liquid drug infusion apparatus that is worn by a patient comprising:
   (a) hollow shell means having a liquid drug outlet port;
   (b) a collapsible liquid drug container housed within the shell means, the interior of the container being connected to the liquid drug outlet port of the shell means;
   (c) a valve in said liquid drug outlet port that is normally closed when the cartridge is not in combination with the liquid drug infusion apparatus and is normally open when the cartridge is in combination with the liquid drug infusion apparatus;
   (d) pressure means within the shell means for maintaining a substantially constant positive pressure on the liquid drug within the container;
   (e) means for indicating the volume of liquid drug within the container comprising a visible indicator on said container and a visible volume scale on said shell, the indicator being adapted to move relative to the scale as the container collapses whereby the indicator cooperates with the scale to indicate said volume; and
   (f) lock means on the exterior of the shell means for reversibly interlocking the cartridge to the drug infusion apparatus.

2. The cartridge of claim 1, wherein said collapsible liquid drug container has a bellows configuration.

3. The cartridge of claim 1, wherein said collapsible liquid drug container is an elastomeric, axially and radially distensible bladder.

4. The cartridge of claim 3 wherein the pressure means is the elastic force inherent in the walls of the bladder.

5. The cartridge of claim 1 wherein the pressure means is a portion of liquid that has a vapor pressure greater than atmospheric pressure at the temperature at which the cartridge is used.

* * * * *